(12) United States Patent
Fujita et al.

(10) Patent No.: US 8,011,223 B2
(45) Date of Patent: Sep. 6, 2011

(54) REMAINING HYDROGEN SENSOR

(75) Inventors: Yasuhiro Fujita, Hokkaido (JP);
Yoshinori Kawaharazaki, Hokkaido (JP); Yasushi Owaki, Hokkaido (JP);
Yoshihiko Hayashi, Hokkaido (JP);
Takashi Iwamoto, Hokkaido (JP)

(73) Assignee: The Japan Steel Works, Ltd., Tokyo (JP)

( * ) Notice: Subject to any disclaimer, the term of this patent is extended or adjusted under 35 U.S.C. 154(b) by 50 days.

(21) Appl. No.: 12/517,298

(22) PCT Filed: Jan. 23, 2008

(86) PCT No.: PCT/JP2008/050916
§ 371 (c)(1),
(2), (4) Date: Jun. 2, 2009

(87) PCT Pub. No.: WO2008/090932
PCT Pub. Date: Jul. 31, 2008

(65) Prior Publication Data
US 2010/0050734 A1 Mar. 4, 2010

(30) Foreign Application Priority Data
Jan. 26, 2007 (JP) .................................. 2007-016241

(51) Int. Cl.
*G01N 33/20* (2006.01)
(52) U.S. Cl. ...................................... 73/19.07
(58) Field of Classification Search .................. 73/19.07; 96/108
See application file for complete search history.

(56) References Cited

U.S. PATENT DOCUMENTS

| 6,584,825 | B2 * | 7/2003 | Pratt et al. ...................... 73/23.2 |
| 7,134,317 | B2 * | 11/2006 | Shimada et al. ............... 73/23.2 |
| 2005/0067281 | A1 | 3/2005 | Shimada et al. |
| 2005/0186117 | A1 * | 8/2005 | Uchiyama et al. .............. 422/91 |
| 2006/0266219 | A1 * | 11/2006 | Ovshinsky et al. ............. 96/108 |
| 2009/0107853 | A1 * | 4/2009 | Tan et al. ........................... 206/7 |

FOREIGN PATENT DOCUMENTS

| JP | 59-78902 A | 5/1984 |
| JP | 1-28341 B2 | 6/1989 |

(Continued)

OTHER PUBLICATIONS

"Invar" Alloy Digest. Filing Code: Fe-24 Iron Alloy. Published by Engineering Alloys Digest, Inc. pp. 1-2. Mar. 1964.*

*Primary Examiner* — Lisa M Caputo
*Assistant Examiner* — Punam Roy
(74) *Attorney, Agent, or Firm* — Sughrue Mion, PLLC

(57) ABSTRACT

In the hydrogen remaining sensor of the present invention, the hydrogen remaining sensor is arranged in a space in which the hydrogen is absorbed/released by the main hydrogen storage alloy, and is equipped with the vessel-like sensor main body in which the sensor hydrogen storage alloy is filled and through which the hydrogen is moved. Also, the easy-to-deform portion in which the strain is caused easily due to the hydrogen absorption/release of the sensor hydrogen storage alloy is provided to a part of the sensor main body, and the strain gauge for measuring the strain of the easy-to-deform portion is provided. As a result, according to the hydrogen remaining sensor of the present invention can contribute to sense precisely a remaining amount of hydrogen in the main hydrogen storage alloy.

9 Claims, 7 Drawing Sheets

FOREIGN PATENT DOCUMENTS

| | | |
|---|---|---|
| JP | 2-140641 A | 5/1990 |
| JP | 2-31004 B2 | 7/1990 |
| JP | 5-19903 U | 3/1993 |
| JP | 6-66787 A | 3/1994 |
| JP | 10-73530 A | 3/1998 |
| JP | 2000-97931 A | 4/2000 |
| JP | 2001-174391 A | 6/2001 |
| JP | 3203062 B2 | 6/2001 |
| JP | 3624816 B2 | 12/2004 |
| JP | 2005-106617 A | 4/2005 |

* cited by examiner (a)

(b)

(c)

(a)  (b)

(a)

(b)

REMAINING HYDROGEN SENSOR

TECHNICAL FIELD

The present invention relates to a hydrogen remaining sensor for sensing an amount of remaining hydrogen in a hydrogen storage vessel, or the like that contains a hydrogen storage alloy.

BACKGROUND ART

The technology to utilize a hydrogen storage alloy, which can store hydrogen compactly at a low pressure, as a hydrogen source of a hydrogen utilizing equipment as typified in a fuel cell is developed. Also, the development of the device, which informs of a remaining quantity of hydrogen, like a remaining indicator of a battery or a gasoline tank is advanced in parallel such that the user can know a remaining hydrogen in the hydrogen storage vessel.

For example, in Patent Literature 1, the device in which an increase in volume of the hydrogen storage alloy in a chamber via a filter is converted into an electric signal to calculate a degree of hydrogen reaction has been proposed. However, this device has such drawbacks that 1) a size of the sensor is needed to some extent, 2) it is difficult to attain a size reduction, 3) an output is easily changed depending on a direction of the vessel, 4) a volume is varied along with the progress of pulverization of the hydrogen storage alloy, and the like.

In Patent Literatures 2, 3, 4, the device in which an electrode is arranged to both ends of the hydrogen-storage-alloy filling portion and then a remaining hydrogen is sensed in response to a change of an electric resistance value has been proposed. However, in fact the obtained electric resistance value depends on a contact density between powders of the hydrogen storage alloy. Therefore, this device also has such drawbacks that an output is easily changed depending on the pulverization of the hydrogen storage alloy or the direction of the vessel, like the above device.

Also, in Patent Literature 5, the hydrogen remaining meter in which hydrogen storage alloys whose plateau pressure is different respectively are put in a vessel and stepwise changes of a pressure are regarded as changes of remaining hydrogen has been proposed. In Patent Literature 6, the hydrogen remaining meter in which pressure/temperature of a vessel are applied to a PCT characteristic diagram of the hydrogen storage alloy to calculate an amount of absorbed hydrogen has been proposed. These hydrogen remaining meters are sufficiently effective if a temperature gradient is hardly present in the overall vessel containing the hydrogen storage alloy and a hydrogen pressure is in a gas-solid equilibrium. However, in most cases the pressure/temperature are in a transient state under the actual using conditions, and thus it is very difficult to calculate a precise amount of remaining hydrogen by the above method. Also, a sensing precision of remaining hydrogen is worsened much more when the pressure enters into a plateau area. In addition, sensors for measuring a temperature and a pressure must be provided, and therefore the device is increased in space and weight.

Also, in Patent Literature 7, the device in which a strain gauge is stuck on a wall of the hydrogen storage vessel and a remaining hydrogen is sensed in response to a change of output has been proposed. The drawbacks of this device are given as two points. That is, (1) a distribution of the hydrogen storage alloy is changed when the direction of the vessel is changed and thus a strain output is also changed at the same hydrogen absorption amount, so that reproducibility of a hydrogen remaining value become worse. (2) In order to correlate a hydrogen remaining state of 0% to 100% with a strain output of the vessel wall on a one-to-one basis, an inflation stress must be applied to an inner wall of the vessel from an initial stage of absorption, so that the device cannot be implemented unless a filling density of the hydrogen storage alloy should be increased considerably high. However, a plastic deformation or a fracture of the vessel is caused without fail at such filling density of the hydrogen storage alloy. But then a range in which the hydrogen storage alloy exerts a pressure on the inner wall of the vessel is restricted in a high hydrogen capacity range when the filling density of the hydrogen storage alloy is lowered. As a result, a change of strain in an essential low hydrogen remaining range cannot be sensed.

Patent Literature 1: JP-B-1-28341
Patent Literature 2: JP-B-2-31004
Patent Literature 3: Japanese Patent No. 3624816
Patent Literature 4: JP-A-2000-97931
Patent Literature 5: JP-A-59-78902
Patent Literature 6: JP-A-2-140641
Patent Literature 7: Japanese Patent No. 3203062

DISCLOSURE OF THE INVENTION

Problems that the Invention is to Solve

As described above, the hydrogen remaining meters in the prior art have such problems that a size is too large to install into a small-sized hydrogen storage vessel, an output is ready to change depending upon the using conditions, and it is difficult to sense a remaining hydrogen in a practical use range. Therefore, there exists such a problem that it is difficult to put the meters to practical use.

The present invention has been made with the above circumstances as a background, and it is an object of the present invention to provide a hydrogen remaining sensor whose size reduction can be achieved, whose output is stable irrespective of using conditions, and which is capable of sensing precisely a remaining hydrogen in a practical use range.

Means for Solving the Problems

That is, a hydrogen remaining sensor of the present invention arranged in a space in which hydrogen is absorbed/released by a main hydrogen storage alloy, includes a vessel-like sensor main body in which a sensor hydrogen storage alloy is filled and through which the hydrogen is moved; wherein an easy-to-deform portion in which a strain is caused easily due to a hydrogen absorption/release of the sensor hydrogen storage alloy is provided to a part of the sensor main body, and a strain gauge for measuring a strain of the easy-to-deform portion is provided.

Also, in the hydrogen remaining sensor of the present invention, the sensor hydrogen storage alloy is molded at a high density and filled in the sensor main body.

Also, in the hydrogen remaining sensor of the present invention, the sensor main body has a cylinder shape and has a notched portion in a cylinder wall to extend over a full length in an axis direction, and a cylinder wall opposing to the notched portion configures the easy-to-deform portion.

Also, in the hydrogen remaining sensor of the present invention, the sensor main body has a thin wall portion whose wall thickness is thin partially, and the thin wall portion configures the easy-to-deform portion.

Also, in the hydrogen remaining sensor of the present invention, the sensor main body has a weak wall portion whose strength is weak partially, and the weak wall portion configures the easy-to-deform portion.

Also, in the hydrogen remaining sensor of the present invention, the sensor main body has an Invar material as a constituent material.

Also, in the hydrogen remaining sensor of the present invention, a thermal conduction extending portion that extends to an outside is provided to the sensor main body, and the thermal conduction extending portion is arranged to contact a hydrogen storage alloy side.

Also, in the hydrogen remaining sensor of the present invention, the sensor main body is fixed to an attached member of a hydrogen storage vessel that contains the main hydrogen storage alloy therein, and an output line of the strain gauge is provided toward an outer portion of the hydrogen storage vessel through a conduit port that is provided in the attached member.

According to the present invention, the easy-to-deform portion is provided to the sensor main body that is shaped into the vessel. Therefore, the strain generated by expansion/contraction caused due to absorption/release of the hydrogen is concentrated on the easy-to-deform portion, and the strain of the easy-to-deform portion is measured precisely by the strain gauge. A correlation is present between the hydrogen absorption/release of the sensor hydrogen storage alloy and the strain caused in the sensor main body in which the sensor hydrogen storage alloy is filled. When the sensor hydrogen storage alloy absorbs a larger amount of hydrogen, this alloy expands and thus a load applied to the sensor main body is increased. Therefore, an amount of strain caused in the easy-to-deform portion is increased correspondingly.

Also, an amount of hydrogen absorbed in the sensor hydrogen storage alloy has a correlation with a hydrogen equilibrium pressure in the space the hydrogen remaining sensor is arranged, i.e., a hydrogen remaining amount. Therefore, a correlation is recognized between an amount of strain measured by the strain gauge and a hydrogen remaining amount. As a result, a hydrogen remaining amount can be known based on an amount of measured strain.

In this case, as the easy-to-deform portion of the sensor main body, any portion may be employed if such portion can produce easily the strain relatively to other portion of the sensor main body. Ease in producing the strain is not requested as an absolute quantity, and an extent of difference from other portions is not particularly restricted. The easy-to-deform portion can be provided to a part of the sensor main body by adjusting the shape, material, or characteristic of the sensor main body. The easy-to-deform portion may be formed not only at a single location but also at plural locations.

Also, the hydrogen remaining sensor is arranged in the space in which the absorption/release of the hydrogen is done by the main hydrogen storage alloy. The arranged position is not particularly restricted. The hydrogen remaining sensor may be arranged in the inside of the hydrogen storage vessel in which the main hydrogen storage alloy is contained, the moving path of hydrogen, or the space communicated with these spaces. Namely, any space may be employed if the hydrogen can move through the space along with the hydrogen absorption/release caused by the main hydrogen storage alloy.

Also, in the present invention, the strain gauge for measuring the strain of the easy-to-deform portion is not particularly restricted in type, structure, etc. Any gauge may be employed if such gauge can measure the strain and output the measured result, and also the already-known gauge can be employed.

Also, it is desirable that the sensor main body should have a small thermal expansion in transferring a heat generated due to the absorption/release of hydrogen. When the sensor main body have a large thermal expansion, an amount of stain to be measured in the strain measurement is affected by the thermal expansion of the sensor main body and thus accuracy of the measurement is lowered. Here, an amount of stain can be corrected by taking account of the influence of this thermal expansion. In this case, it is desirably that the Invar whose thermal expansion coefficient is small should be used as the constituent material of the sensor main body. The Invar whose average thermal expansion coefficient is $5 \times 10^{-6}$ or less in a temperature range of 0 to 50° C. may be pointed out. Commonly the Invar is formed of Ni, Fe as principal components. In the present invention, component and composition ranges are not restricted to particular ones. Also, when the sensor main body is formed of the Invar, such a mode may be contained in a range of the above mode that the material other than the Invar is used as the easy-to-deform portion, or the like.

In the sensor main body, as described above, the easy-to-deform portion can be provided to a part of the sensor main body by adjusting the shape, material, characteristic, or the like of the sensor main body. As the adjustment of shape, the easy-to-deform portion can be formed by providing the notched portion in the sensor main body, for example. When the sensor main body is formed like a cylinder shape such as a circular cylinder, a square cylinder, or the like and then the notched portion is provided in the cylinder wall over a full length in the axis direction, the sensor main body can be deformed to open outward at the notched portion in the cylinder wall. As a result, the easy-to-deform portion can be obtained in the cylinder wall on the opposite side opposing to the notched portion. Also, when a wall thickness of a part of the sensor main body is thinned, strength of the thin wall is lowered and thus the easy-to-deform portion can be obtained. Also, when strength of a part of the sensor main body is lowered by differentiating the characteristics, or the like, the easy-to-deform portion can be obtained in the weak strength portion. In the weak strength portion, the strength may be lowered by using the different material, or the strength may be lowered by differentiating partially the heat treatment, or the like.

Also, it is desirable that, since the heat transfer is caused when the hydrogen absorption/release is performed by the main hydrogen storage alloy, the similar heat transfer should be made in the hydrogen remaining sensor. When the hydrogen remaining sensor is positioned apart from the main hydrogen storage alloy, it is feared that the heat transfer similar to that in the main hydrogen storage alloy should not be caused in the hydrogen remaining sensor. Therefore, the thermal conduction extending portion that extends to the outside is provided to the sensor main body, and then this thermal conduction extending portion is joined to the main hydrogen storage alloy side. As a result, the heat transfer similar to that in the main hydrogen storage alloy can be executed on the hydrogen remaining sensor side, and the remaining hydrogen sensing can be made more precisely. In this case, the thermal conduction extending portion may be brought into direct contact with the hydrogen storage alloy by the insertion, or the like, otherwise the thermal conduction extending portion may be brought into contact with the portion where the heat exchange with the hydrogen storage alloy is done.

Advantages of the Invention

As described above, the hydrogen remaining sensor of the present invention arranged in a space in which hydrogen is absorbed/released by a main hydrogen storage alloy, includes a vessel-like sensor main body in which a sensor hydrogen storage alloy is filled and through which the hydrogen is moved; wherein an easy-to-deform portion in which a strain is caused easily due to a hydrogen absorption/release of the sensor hydrogen storage alloy is provided to a part of the sensor main body, and a strain gauge for measuring a strain of the easy-to-deform portion is provided. Therefore, an amount of remaining hydrogen in the main hydrogen storage alloy can be sensed precisely. In addition, following advantages can be listed in the above sensing.

(1) The output value of the remaining amount is not changed depending upon a direction of the sensor main body.

(2) Since the hydrogen storage alloy is filled in the sensor main body at a high density, the hydrogen remaining sensor of the present invention can handle the low remaining area in which the hydrogen remaining meter in the prior art is hard to measure.

(3) Since the sensor main body can be formed in the several mm square and also the strain converting/remaining amount displaying portion can be formed in the several cm square, the hydrogen remaining sensor of the present invention can be formed compactly to respond to the portable type.

DESCRIPTION OF REFERENCE NUMERALS AND SIGNS

Figure 1:
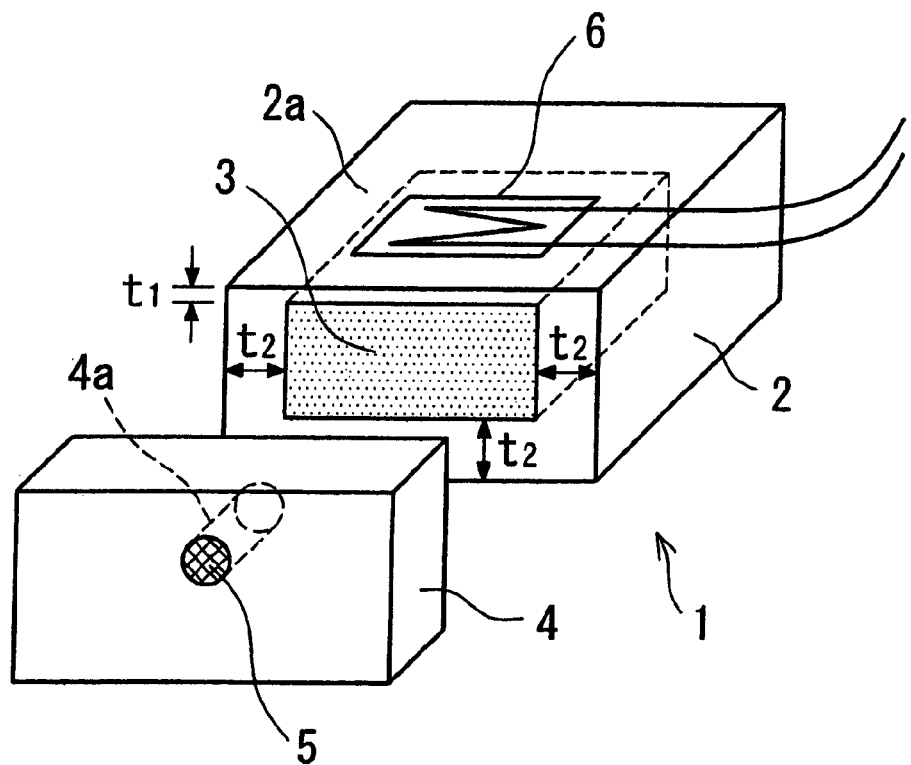
FIG. 1 An exploded perspective view showing a sensor main body of a close square cylinder type of a hydrogen remaining sensor in an embodiment of the present invention.

1 sensor main body
2*a* easy-to-deform portion
3 sensor hydrogen-storage-alloy filling portion
6 strain gauge
6*a* strain output line
10 sensor main body
11*a* easy-to-deform portion
20 sensor main body
20*a* easy-to-deform portion
21 notched portion
23 sensor main body
23*a* easy-to-deform portion
24 notched portion
26 sensor main body
26*a* easy-to-deform portion
27 notched portion
30 thermal conduction extending portion
40 main hydrogen-storage-alloy filling portion
50 attached member
51 conduit port

BEST MODE FOR CARRYING OUT THE INVENTION

Embodiments of the present invention will be explained with reference to the accompanying drawings hereinafter.

First, a main body of a hydrogen remaining sensor formed of a small vessel will be explained hereunder. A size of the sensor main body is not particularly mentioned. A size of several square mm is preferable because the sensor is put easily in a small-sized hydrogen storage vessel and the devising to attach a valve that controls the absorption/release of hydrogen, or the like is easily applied.

As the vessel material of the sensor main body, any metal such as aluminum, various steels, or the like may be employed if such metal has adequate strength and elasticity. In this case, the material such as high carbon steel, titanium, or the like, which has hydrogen brittleness, is not preferable because it is feared that its strength is changed in use. The Invar such as Fe-36Ni, or the like has a small thermal expansion coefficient and thus can reduce the influence of output error due to a temperature change. Also, though the material such as a resin, or the like other than the metal is used as the material of the sensor main body, no trouble is caused if strength and elasticity meet the conditions.

It is common that, as the hydrogen storage alloy for the sensor filled in the sensor main body, the same alloy as the hydrogen storage alloy contained in the hydrogen storage vessel of a remaining hydrogen measured object (main hydrogen storage alloy) should be employed. But a hydrogen storage alloy different from the main hydrogen storage alloy may be filled if the characteristic that enables the sensor to sense more precisely the remaining hydrogen can be obtained. The hydrogen storage alloy for the sensor is chosen from a group of alloys that can storage a large volume of hydrogen in compact at a low pressure and can absorb/release the hydrogen reversibly. Preferably, $AB_5$ type whose basic composition is $LaNi_5$, $AB_2$ type whose basic composition is $TiMn_2$ or $TiCr_2$, $A_2B$ type whose basic composition is $Mg_2Ni$, AB type whose basic composition is TiFe, BCC type whose basic composition is TiCrV, or the like may be listed. All alloys have the property that expands when the alloy absorbs the hydrogen while contracts when the alloy releases the hydrogen.

Also, shapes of the sensor main body are classified into a close type vessel shape and an, for example.

In the close type, the hydrogen storage alloy is filled in a cavity provided in the vessel as the sensor main body and then a lid is joined to the vessel. A clearance or a filter through which only a hydrogen gas can pass but powders of the hydrogen storage alloy do not flow out is provided to the vessel main body or the lid. As a means for concentrating an expansion stress of the hydrogen storage alloy in the close type sensor main body, a sensor main body 1 having a square cylinder structure with bottom, as shown in FIG. 1, for example, may be considered. The sensor main body 1 has a vessel 2 whose one surface side is opened, and a lid 4 for covering an opening portion of the vessel 2. A through hole 4a through which the hydrogen can pass is provided to the lid 4, and a filter 5 is arranged in this through hole 4a. The inside of this square cylinder constitutes a sensor hydrogen-storage-alloy filling portion 3, and the hydrogen storage alloy provided in a powder state or molded at a high density is filled therein. A thickness of the vessel 2 surrounding the sensor hydrogen-storage-alloy filling portion 3 is thinned intentionally only on one surface (upper wall in FIG. 1) ($t_1 < t_2$), and a great strain appears on this surface when the hydrogen storage alloy expands along with the hydrogen absorption. That is, the wall of this surface acts as an easy-to-deform portion 2a. When a strain gauge 6 is stuck onto this easy-to-deform portion 2a, an expansion stress, i.e., a hydrogen absorption ratio of the hydrogen storage alloy, can be obtained as an output of the strain gauge.

Figure 2:
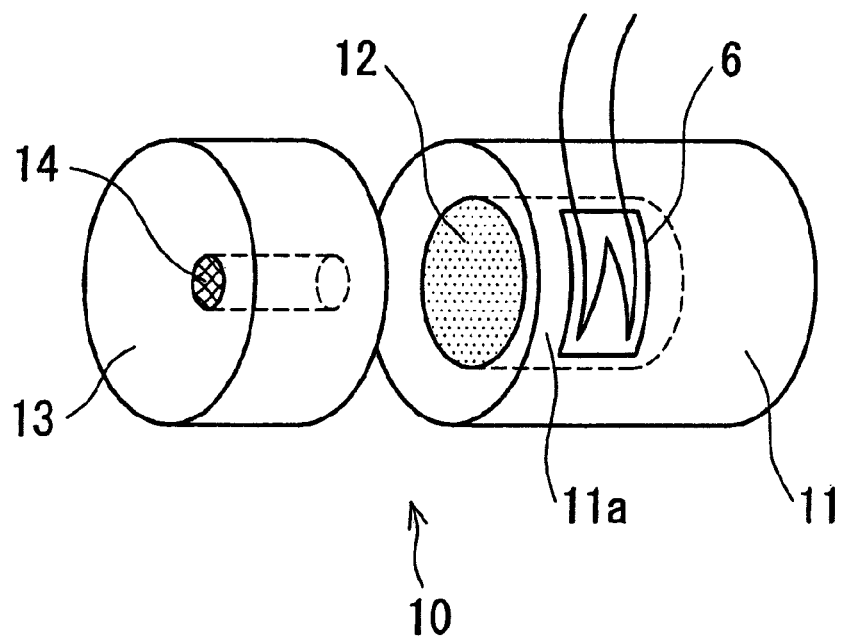
FIG. 2 An exploded perspective view showing a sensor main body of a close circular cylinder type of a hydrogen remaining sensor in another embodiment of the present invention.

A sensor main body 10 of circular cylinder type is shown in FIG. 2. In this example, one end surface of a vessel 11 having a circular cylinder shape with bottom is opened in the axis direction, a lid 13 is covered on this opening portion. A through hole through which the hydrogen can pass in the similar mode to the above is provided in the lid 13. A filter 14 is arranged in this through hole. A sensor hydrogen-storage-alloy filling portion 12 having a circular column hole shape is formed in the vessel 11 in an eccentric manner. The cylinder wall portion whose thickness is thinned constitutes an easy-to-deform portion 11a. The strain gauge 6 is stuck on an outer surface of this easy-to-deform portion 11a.

Next, the sensor main body having the open type vessel shape will be explained hereunder. In a hydrogen remaining sensor having a sensor main body of this type, the sensor main body itself is shaped to act as a spring such that an expansion stress caused in the hydrogen storage alloy is transferred effectively to a strain gauge.

Figure 3:
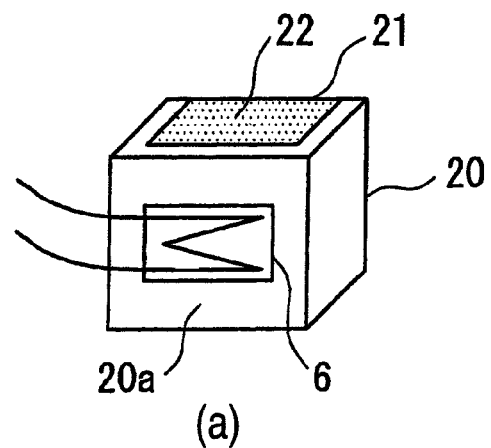
FIG. 3 A perspective view showing a sensor main body of an open type (U-shaped type, C-shaped type, triangular cylinder type) of a hydrogen remaining sensor in still another embodiment of the present invention.
Figure 3:
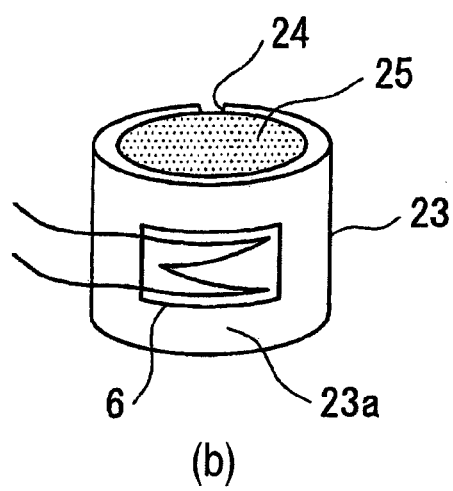
Figure 3:
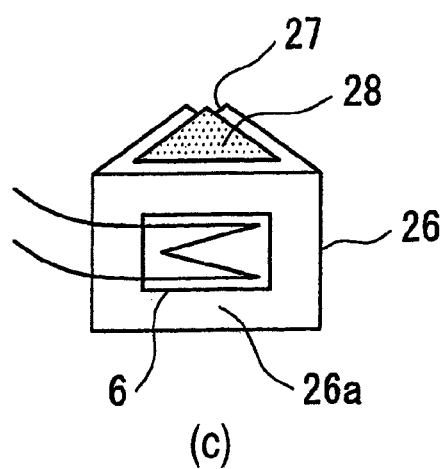

For example, a square cylinder type sensor main body 20 shown in FIG. 3(a), a circular cylinder type sensor main body 23 shown in FIG. 3(b), or a triangular cylinder type sensor main body 26 shown in FIG. 3(c) may be considered. A notched portion 21, a notched portion 24, and a notched portion 27 that extend over the axis direction are formed in the cylinder wall of the sensor main body respectively. In the sensor main body 20, one side wall of four square cylinder walls is notched as the notched portion 21 to have a U-shape in section, and the inside of the square cylinder constitutes a sensor hydrogen-storage-alloy filling portion 22. Also, in the sensor main body 23, a part of the circular cylinder is notched as the notched portion 24 over a full length in the axis direction to have a C-shape in section, and the inside of the circular cylinder constitutes a sensor hydrogen-storage-alloy filling portion 25. Also, in the sensor main body 26, one apex portion of the triangular cylinder walls is notched as the notched portion 27 over a full length in the axis direction, and the inside of the triangular cylinder constitutes a sensor hydrogen-storage-alloy filling portion 28. The cylinder walls opposing to these notched portions constitute an easy-to-deform portion 20a, an easy-to-deform portion 23a, and an easy-to-deform portion 26a on which the stress is concentrated when respective sensor main bodies 20, 23, 26 are deformed while using the notched portions 21, 24, 27 as the open end respectively.

In such open type structure, because the exposure of the hydrogen storage alloy is inevitable, such a situation must be prevented that the hydrogen storage alloy comes out from the sensor main body. As the measure to prevent such a situation, the method of shaping the hydrogen storage alloy to fit into the sensor main body, the method of covering the exposed surface of the hydrogen storage alloy with an elastic resin, and the like may be considered. In these structures, the opposite side to the notched portion constitutes the easy-to-deform portion in which a strain appears most easily when the hydrogen storage alloy expands/contracts, and therefore the strain gauge 6 is stuck on the surface of that portion.

Figure 4:
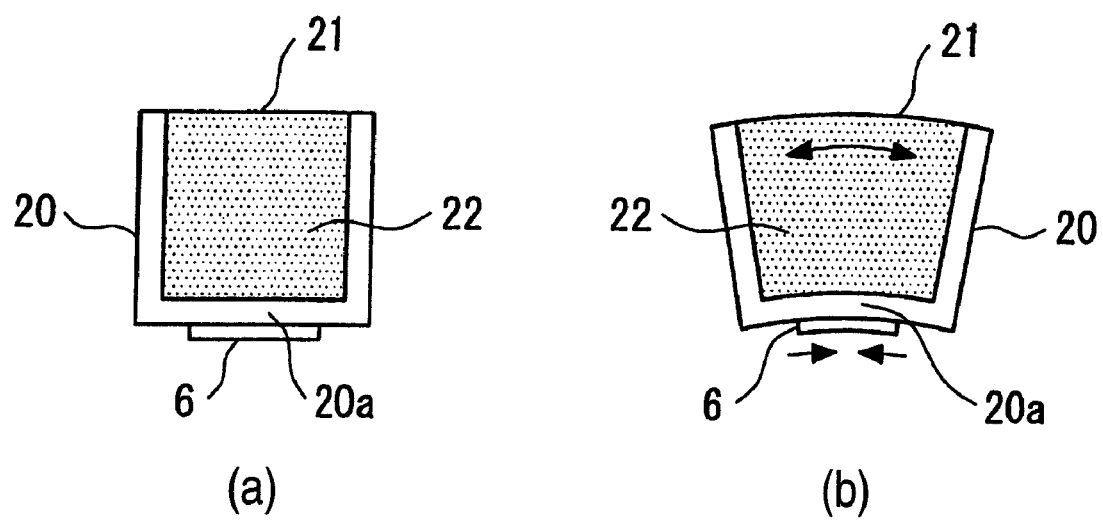
FIG. 4 A schematic view showing a deformation caused due to the hydrogen absorption/release in the sensor main body of the open type (U-shaped type) of the hydrogen remaining sensor of the present invention.

A schematic view of a deformation caused due to the hydrogen absorption/release in the sensor hydrogen-storage-alloy filling portion 22 of the sensor main body 20 of the U-shaped open type is shown in FIG. 4. When the hydrogen storage alloy absorbs the hydrogen and expands, the sensor main body 20 is deformed elastically to open the open end of the notched portion 21. Therefore, a strain is concentrated on the easy-to-deform portion 20a located on the opposite side to the open end, and the strain gauge 6 undergoes a compressive stress. A strain of the easy-to-deform portion 20a is sensed by the strain gauge 6.

In this case, it is preferable that a filling density of the hydrogen storage alloy in the sensor main body in this mode should be set as high as possible within such a range that the elastic deformation of the sensor main body is allowed. As the means for increasing a filling density, in addition to the method of packing the powders of the hydrogen storage alloy in the sensor main body, the method of employing the material in which the powders of the hydrogen storage alloy and a silicon resin, etc. are mixed and then molded by the compression molding, the method of employing the composite material in which the powders of the hydrogen storage alloy and powders of soft metal are mixed and then molded by the pressing, and the like may be considered. When an occupation ratio of the hydrogen storage alloy to a volume of the hydrogen storage alloy filling space in the sensor main body exceeds 50%, a change of strain is easy to appear even in the stage in which a hydrogen absorption ratio is low, and thus such situation is preferable on the performance of the hydrogen remaining meter.

In this case, the main hydrogen storage alloy is filled in the inside of the hydrogen storage vessel (not shown), and also a filter, a ventilating material, a heat transmission facilitating material, etc. are arranged appropriately in the inside. From such a viewpoint that preciseness should be ensured in a hydrogen remaining output, it is preferable that the sensor main body of the hydrogen remaining sensor should be arranged around a center of the main hydrogen-storage-alloy filling portion such that a temperature of the sensor hydrogen storage alloy of the hydrogen remaining sensor coincides as closely as possible with a temperature of the main hydrogen storage alloy.

Figure 5:
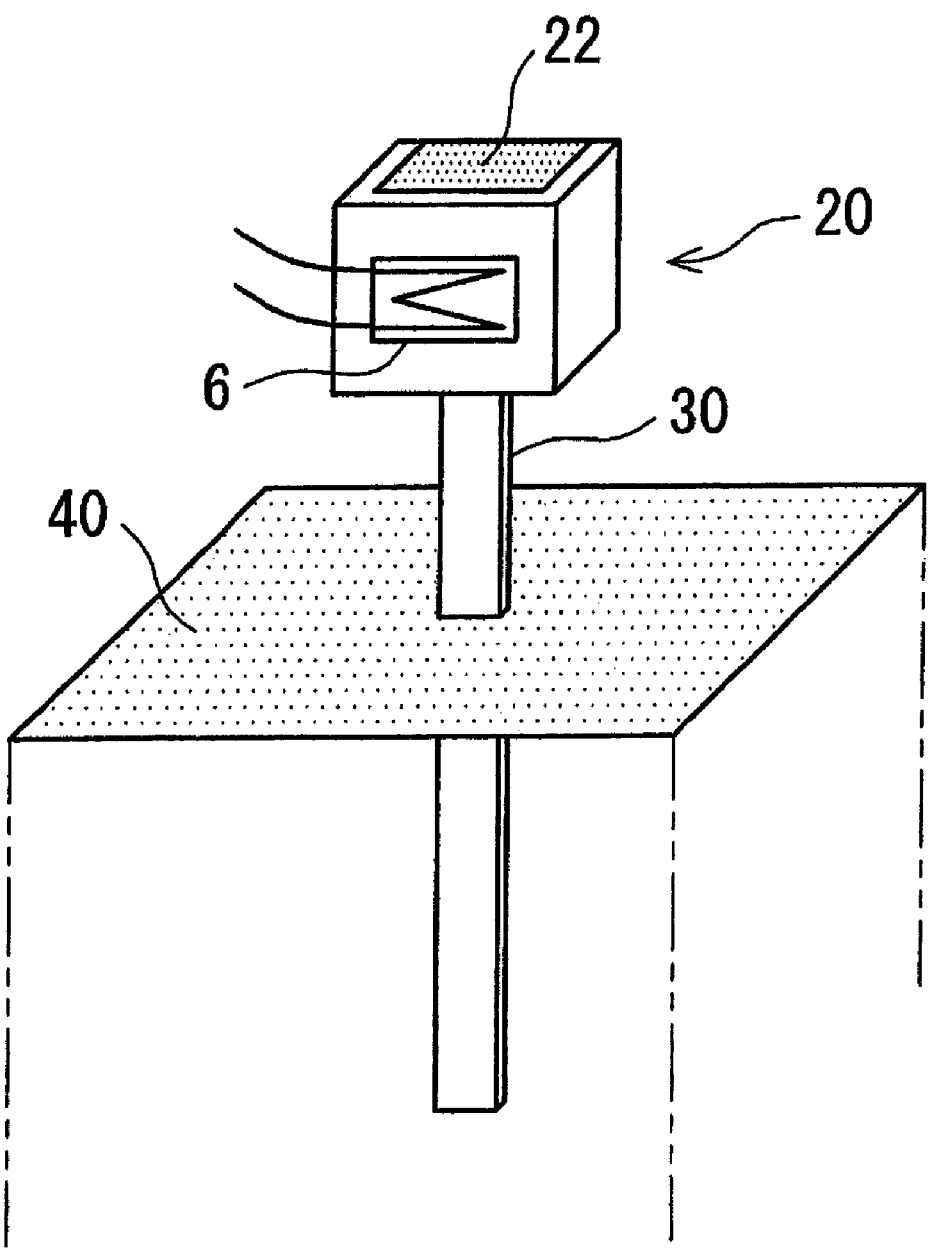
FIG. 5 A view showing yet still another embodiment of the present invention in which a thermal conduction extending portion is provided to a sensor main body.

Further, as shown in FIG. 5, such a method may be employed that a thermal conduction extending portion 30 formed of the material having a good thermal conductance is connected to the sensor main body 20 and one end side of this thermal conduction extending portion 30 is inserted into a main hydrogen-storage-alloy filling portion 40, so that the temperature of the sensor main body may be caused to follow the temperature of the main hydrogen storage alloy.

Figure 6:
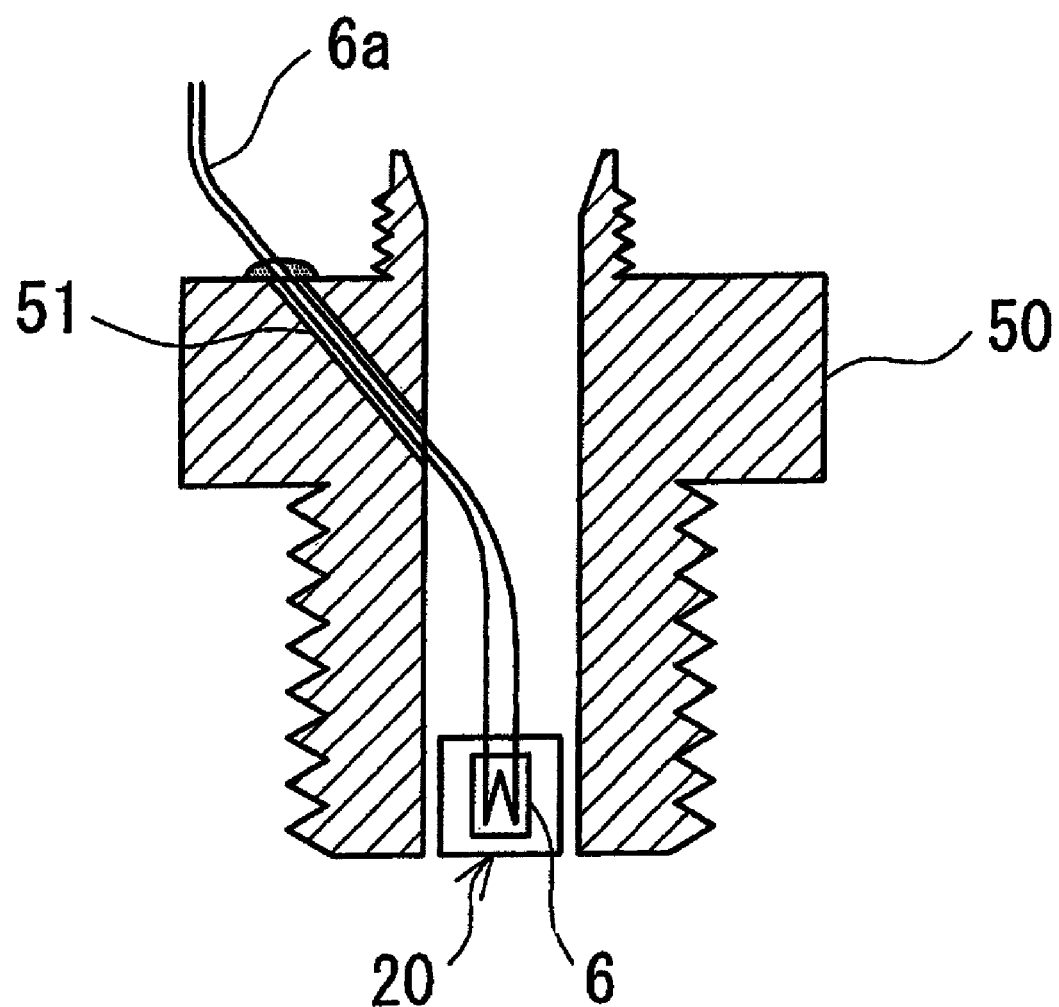
FIG. 6 A view showing a further embodiment of the present invention in which a sensor main body is fixed to a joint as an attached member of a hydrogen storage vessel and a conduit port of a strain gauge output line is provided in the joint.

Also, in the application in which an amount of consumed hydrogen per time is smaller than an amount of stored hydrogen, the remaining output that is precise to some extent can be expected, for a large difference of temperature is not caused between the sensor main body and the main hydrogen storage alloy unless both materials do not directly or indirectly come into contact with each other. At this time, as shown in FIG. 6, when the sensor main body 20 is fixed to an attached member 50 such as a joint, a valve, a safety unit, or the like attached to the hydrogen storage vessel, the assembling operation of the vessel can be simplified. Also, when a conduit port 51 that is communicated between the inside and the outside is provided in the attached member 50, a strain output line 6a can be led to the outside through this conduit port 51 without a dedicated picking joint. In this case, this conduit port 51 is sealed to prevent a leakage of the hydrogen after the strain output line 6a is led.

In FIGS. 5, 6, explanation is made by using the sensor main body 20. But it is of course that the type of the sensor main body is not restricted to the above.

Figure 7:
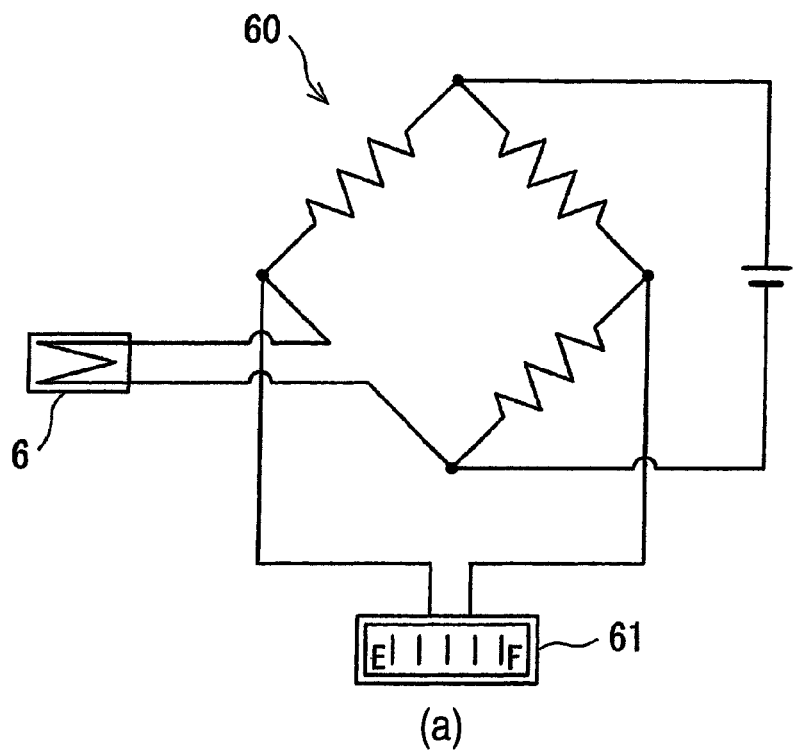
FIG. 7 Circuit diagrams showing a hydrogen remaining indicator of the present invention in which a remaining displaying portion is provided respectively.
Figure 7:
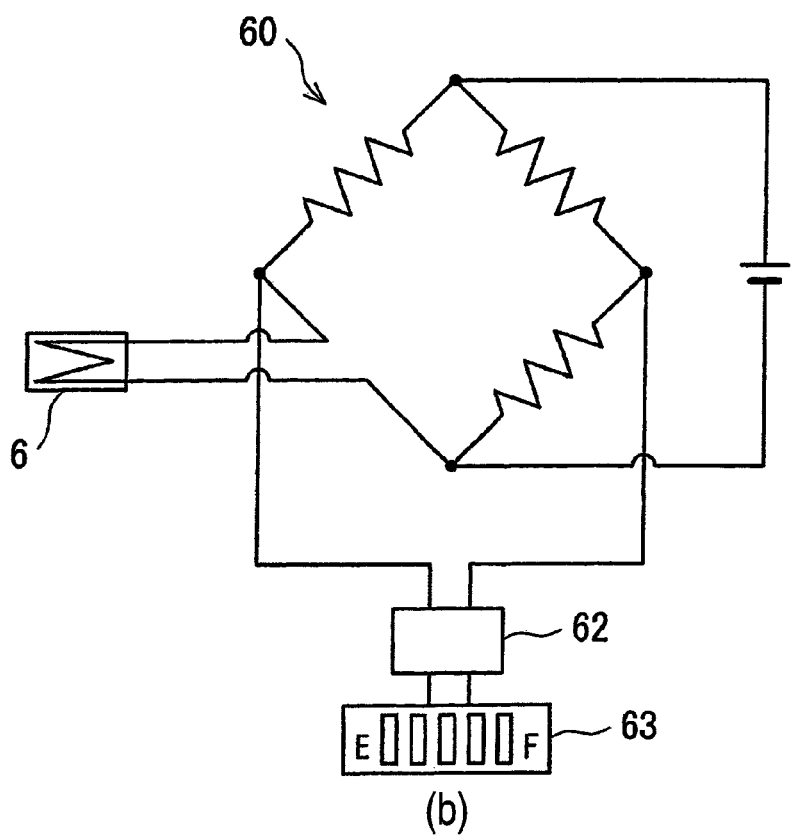

For example, as shown in FIG. 7, a bridge circuit 60 that responds to an electric resistance value of the strain gauge 6 is prepared on the outside of the hydrogen storage vessel. This bridge circuit 60 converts a resistance change caused due to the strain into a voltage change. As shown in FIG. 7(a), the voltage change may be used to output a remaining value on an analog gauge 61. Besides, the voltage change may be converted into a digital signal via an A/D converter 62, and then used to display a remaining hydrogen in the multi-level way by an indicator 63 using the liquid crystal, the LED, or the like. Also, external terminals for analog/digital outputs may be provided, and a remaining signal may be sent out to the connected equipment.

The above circuit can be installed into an area of several square cm. Therefore, when the hydrogen remaining sensor is fitted to a portable hydrogen storage vessel, the remaining sensing/displaying portion including a power source (a dry cell, or the like) as a driving power source can be installed into a minute space. In this case, it is preferable that, since a driving time of the dry cell is limited, such a power consumption saving devising should be applied that buttons are provided respectively, a voltage is applied to the circuit to sense a remaining amount only when the button is pressed, and the hydrogen remaining amount is displayed only for a predetermined time.

Example 1

An example of the present invention will be explained hereunder.

In order to form the same shape as that in FIG. 3(a), a cube (one side is 10 mm) whose three surfaces are formed of an aluminum alloy of 1 mm thick was employed as the sensor main body of the hydrogen remaining sensor. Also, the thermal conduction extending portion (10 mm×40 mm×1 mm) formed of the aluminum alloy was joined to the sensor main body. The material in which the powders of the $AB_5$-based hydrogen storage alloy is mixed with a silicon resin by 5 wt % and then molded was filled at a 60% volume density of the hydrogen storage alloy in the sensor main body (a mass of the hydrogen storage alloy was 3.5 g). A mixture of the hydrogen storage alloy and the resin was filled, and then a strain gauge, KFG typed, manufactured by Kyowa Electronic Instruments Co., Ltd. was stuck in the same position.

The powders of the hydrogen storage alloy, which is the same as that filled in the sensor main body, was filled in the hydrogen storage vessel (an inner volume was 50 cc) for a test by 100 g, and then the thermal conduction extending portion was inserted into the area around the center of main hydrogen-storage-alloy filling portion. Also, the ceramic wool was filled in the clearance portion around the sensor main body. The output line of the strain gauge was extended to the outside through the joint, and was connected to the data collecting device to record the data at any time. Also, the hydrogen introducing valve was fitted to the hydrogen storage vessel.

The hydrogen storage vessel was evacuated into vacuum by a rotary pump for 10 hour at 80° C., and the hydrogen of 1 Mpa was introduced dipping the vessel into a water tank at about 10° C. to activate the hydrogen storage alloy. After the activation, the output of the hydrogen storage vessel was stabilized by repeating twice the hydrogen absorption/release. An amount of hydrogen absorbed when the hydrogen of 1 Mpa was filled fully at 20° C. was calculated as 16 NL. Then, when the hydrogen was released to the atmospheric pressure at a rate of 5 NL/min at maximum while keeping 20° C. after the hydrogen of 1 Mpa was filled fully at 20° C., a change of strain was recorded. Similarly, when the hydrogen was released to the atmospheric pressure at 30° C. and 40° C. after the hydrogen was filled fully, a change of strain was recorded. A graph in which a hydrogen absorption ratio of the hydrogen storage vessel is plotted on the abscissa and a strain caused at that time is plotted on the ordinate is shown in FIG. 8.

Figure 8:
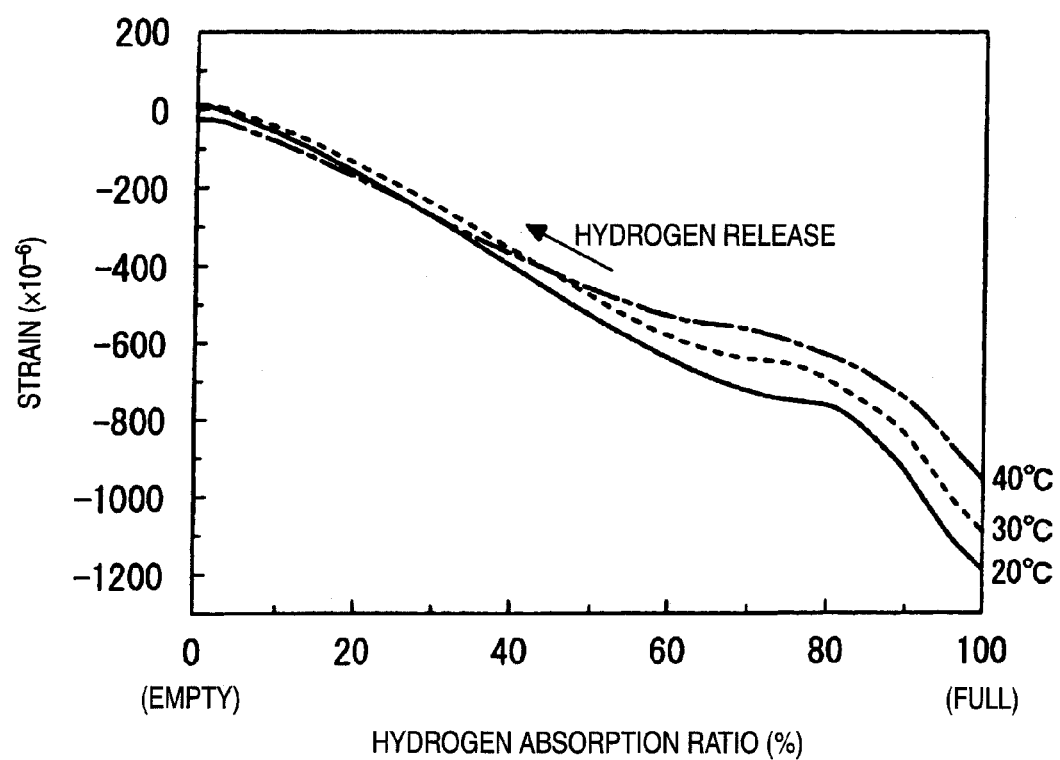
FIG. 8 A graph showing a change of strain output with respect to a hydrogen absorption ratio of the hydrogen remaining sensor in embodiments of the present invention when the hydrogen is released.

As shown in FIG. 8, although a plateau portion appeared slightly around the hydrogen absorption ratio of 60% to 80%, such a tendency was exhibited irrespective of temperature that an amount of strain is increased roughly along a straight line together of the release of the hydrogen (a compressive strain was solved). In particular, a temperature dependency could be reduced in the low hydrogen absorption ratio range, and also a linearity could be increased. As a result, the precise remaining display could be implemented by utilizing this sensor.

The present invention is explained in detail with reference to the particular embodiments. But it is apparent for those skilled in the art that various variations and modifications can be applied without departing from a spirit and a scope of the present invention.

This application is based upon Japanese Patent Application (Patent Application No. 2007-016241) filed on Jan. 26, 2007; the contents of which are incorporated herein by reference.

INDUSTRIAL APPLICABILITY

According to the hydrogen remaining sensor of the present invention, the hydrogen remaining sensor is arranged in a space in which the hydrogen is absorbed/released by the main hydrogen storage alloy, and is equipped with the vessel-like sensor main body in which the sensor hydrogen storage alloy is filled and through which the hydrogen is moved. Also, the easy-to-deform portion in which the strain is caused easily due to the hydrogen absorption/release of the sensor hydrogen storage alloy is provided to a part of the sensor main body, and the strain gauge for measuring the strain of the easy-to-deform portion is provided. As a result, according to the hydrogen remaining sensor of the present invention can contribute to sense precisely a remaining amount of hydrogen in the main hydrogen storage alloy.

The invention claimed is:

1. A hydrogen sensor, the sensor comprising:
a sensor main body configured to contain a sensor hydrogen storage alloy,
wherein the sensor main body comprises a deformable portion, the deformable portion deforms more in response to a hydrogen absorption/release of the sensor hydrogen storage alloy than other portions of the sensor main body, and a strain gauge for measuring a strain is provided on the deformable portion of the sensor main body,
wherein the sensor main body has a cylinder shape and has a notched portion in a cylinder wall to extend over a full length in an axis direction, and the deformable portion is disposed in a cylinder wall opposing the notched portion.

2. The hydrogen sensor according to claim 1,
wherein the sensor hydrogen storage alloy is molded at a high density and filled in the sensor main body.

3. The hydrogen sensor according to claim 1,
wherein the sensor main body has a thin wall portion whose wall thickness is thin in a portion adjacent to the sensor hydrogen storage alloy, and the thin wall portion corresponds to the deformable portion.

4. The hydrogen sensor according to claim 1,
wherein the deformable portion is formed of a weak wall portion whose strength is less than the other portions of the sensor main body.

5. The hydrogen sensor according to claim 1, further comprising:
a second body filled with a hydrogen storage alloy;
wherein the sensor main body comprises a thermal conduction extending portion that extends from the sensor main body to the hydrogen storage alloy in the second body.

6. The hydrogen sensor according to claim 1, further comprising an elastic resin disposed in the notched portion.

7. The hydrogen sensor according to claim 1, wherein the sensor main body further comprises a through hole extending between the sensor hydrogen storage alloy and an external surface of the sensor body,
wherein a filter is disposed in the through hole.

8. The hydrogen sensor according to claim 1, wherein a ratio of the sensor hydrogen storage alloy to a filling space in the sensor main body exceeds 50%.

9. A hydrogen sensor, the sensor comprising:
a sensor main body configured to contain a sensor hydrogen storage alloy,
wherein the sensor main body comprises a deformable portion, the deformable portion deforms more in response to a hydrogen absorption/release of the sensor hydrogen storage alloy than other portions of the sensor main body, and a strain gauge for measuring a strain is provided on the deformable portion of the sensor main body,
wherein the sensor main body is fixed to an attached member of a hydrogen storage vessel that contains a main hydrogen storage alloy, and an output line of the strain gauge is provided toward an outer portion of the hydrogen storage vessel through a conduit port that is provided in the attached member.

* * * * *